(12) United States Patent
Lester et al.

(10) Patent No.: US 6,183,475 B1
(45) Date of Patent: Feb. 6, 2001

(54) DISTAL FEMORAL OSTEOTOMY SYSTEM AND METHOD

(75) Inventors: Mark Lester; Sam Morgan, both of Austin, TX (US); Mark T. Dahl, Eagan, MN (US)

(73) Assignee: Sulzer Orthopedics Inc., Austin, TX (US)

(*) Notice: Under 35 U.S.C. 154(b), the term of this patent shall be extended for 0 days.

(21) Appl. No.: 09/216,491

(22) Filed: Dec. 18, 1998

(51) Int. Cl.$^7$ .................................................. A61B 17/56
(52) U.S. Cl. ................................................. 606/69; 606/65
(58) Field of Search ................................. 606/69, 70, 71, 606/86, 65, 66

(56) References Cited

U.S. PATENT DOCUMENTS

| 4,096,857 | * | 6/1978 | Cramer et al. | 606/71 |
| 4,651,724 | * | 3/1987 | Berentey et al. | 606/69 |
| 4,988,350 | * | 1/1991 | Herzberg | 606/65 |
| 5,021,056 | | 6/1991 | Hofmann et al. | 606/86 |
| 5,041,116 | * | 8/1991 | Wilson | 606/65 |
| 5,053,039 | | 10/1991 | Hofmann et al. | 606/87 |
| 5,591,168 | * | 1/1997 | Judet et al. | 606/65 |
| 5,613,969 | | 3/1997 | Jenkins, Jr. | 606/87 |
| 5,662,655 | * | 9/1997 | Laboureau et al. | 606/69 |
| 5,674,222 | * | 10/1997 | Berger et al. | 606/69 |

* cited by examiner

Primary Examiner—Michael H. Thaler
Assistant Examiner—Julian W. Woo
(74) Attorney, Agent, or Firm—Philip S. Lyren

(57) ABSTRACT

A distal femoral osteotomy system and method according to which an end segment is cut from the bone to be realigned and a wedge-shaped segment is cut from between the end segment and the remaining portion of the bone. The wedge-shaped segment is cut so that it has an angled surface substantially corresponding to the angle of malalignment. The wedge-shaped segment is discarded and the severed end segment is repositioned relative to the remaining portion of the bone at an angle corresponding to the angle of malalignment to realign the end segment and the remaining bone portion and correct for the malalignment. A compressive load is then established across the remaining bone portion and the end segment.

13 Claims, 2 Drawing Sheets

DISTAL FEMORAL OSTEOTOMY SYSTEM AND METHOD

BACKGROUND

The disclosures herein relate to a distal femoral osteotomy system and method, and, more particularly, to a system and method for correcting for leg bone malalignment using distal femoral osteotomy.

Malalignment of the anatomical axis and the mechanical axis of a leg bone along the tibia and the femur in the coronal plane leads to several problems, including tibial-femoral varus and valgus, and degenerative osteoarthritis of the knee. Previous attempts to correct for this have included an upper tibia osteotomy, according to which a wedge-shaped segment is cut from the upper end portion of the tibia bone. After the segment is removed, an external compressor device is fastened to the bone and draws the osteotomy closed by plastic deformation of the unsevered portion of the bone. The realigned bone portions are then secured by a plate using screw fixation. Examples of this technique are disclosed in U.S. Pat. No. 5,021,056 and U.S. Pat. No. 5,053,039, assigned to the assignee of the present invention, and their disclosures are incorporated by reference.

In U.S. Pat. No. 5,613,969, a surgical kit for performing a tibial osteotomy is provided, comprising a pair of mounting pins for attaching an osteotomy guide in a predetermined relation to a tibia, an osteotomy guide comprising a transverse slot defining a transverse cutting plane adapted to receive and guide a transverse cutting blade for making a transverse cut into the tibia, and a plurality of oblique slots angularly offset from the transverse slot, each oblique slot defining an oblique cutting plane adapted to receive and guide an oblique cutting blade for making a selected oblique cut into the tibia, wherein the intersection of each oblique cutting plane with the transverse cutting plane defines a wedge of bone which may be removed from the tibia. Also included with the surgical kit are a compression clamp adapted to apply compressive forces to a first portion of the tibia above the transverse cut and to a second portion of the tibia below the oblique cut to draw the first and second portions together, and a fixation plate adapted to hold the portions of the tibia together during healing.

Although this type of procedure considerably advanced the art for correcting for leg malalignment by tibia osteotomy, it is recognized that certain malalignment in lateral compartment osteoarthritis is best managed by osteotomy on the distal femur. However, there are several disadvantages to the latter procedure. For example, there is often a mismatching of osteotomy surfaces and a consequent mismatching of cortical margins, providing less stable surfaces to compress against one another. Additionally, the distance of the osteotomy away from the deformity apex creates an additional relative lateral translation of the distal fragment. Thus, the osteotomy must be completed, rather than hinged, on the lateral side, therefore creating an unstable osteotomy. As a result, a plate on the medial side cannot be utilized as in the case of an upper tibial osteotomy. Also, these distal femoral osteotomies often suffer from the fact that they are difficult to reproduce and therefore unpredictable.

SUMMARY

The present embodiments, accordingly, are directed to a distal femoral osteotomy system and method which overcomes the above problems with previous procedures.

To this end, according to the system and method of these embodiments, an end segment is cut from the bone to be realigned, and a wedge-shaped segment is cut from between the end segment and the remaining portion of the bone. The wedge-shaped segment is cut so that it has an angled surface substantially corresponding to the angle of malalignment. The wedge-shaped segment is discarded and the severed end segment is repositioned relative to the remaining portion of the bone at an angle corresponding to the angle of malalignment to realign the end segment and the remaining bone portion and correct for the malalignment. A compressive load is then established across the remaining bone portion and the end segment to allow healing.

This system and method enjoy several advantages. For example, it provides even compressive loading across the osteotomy site and improved bone healing. Also, the system can be left permanently attached as shown and described since it maintains a low profile and thus reduces complications with soft tissue closure and irritation. Further, any mismatching of osteotomy surfaces, and a consequent mismatching of cortical margins, is avoided. Still further, relative lateral translation of the segment and the femur is minimized. Also, the method of the present invention is easy to reproduce and is therefore predictable and can be completed with minimal disturbance to the patella, ligaments, and soft tissue.

BRIEF DESCRIPTION OF THE DRAWING FIGURES

DETAILED DESCRIPTION

Figure 1:
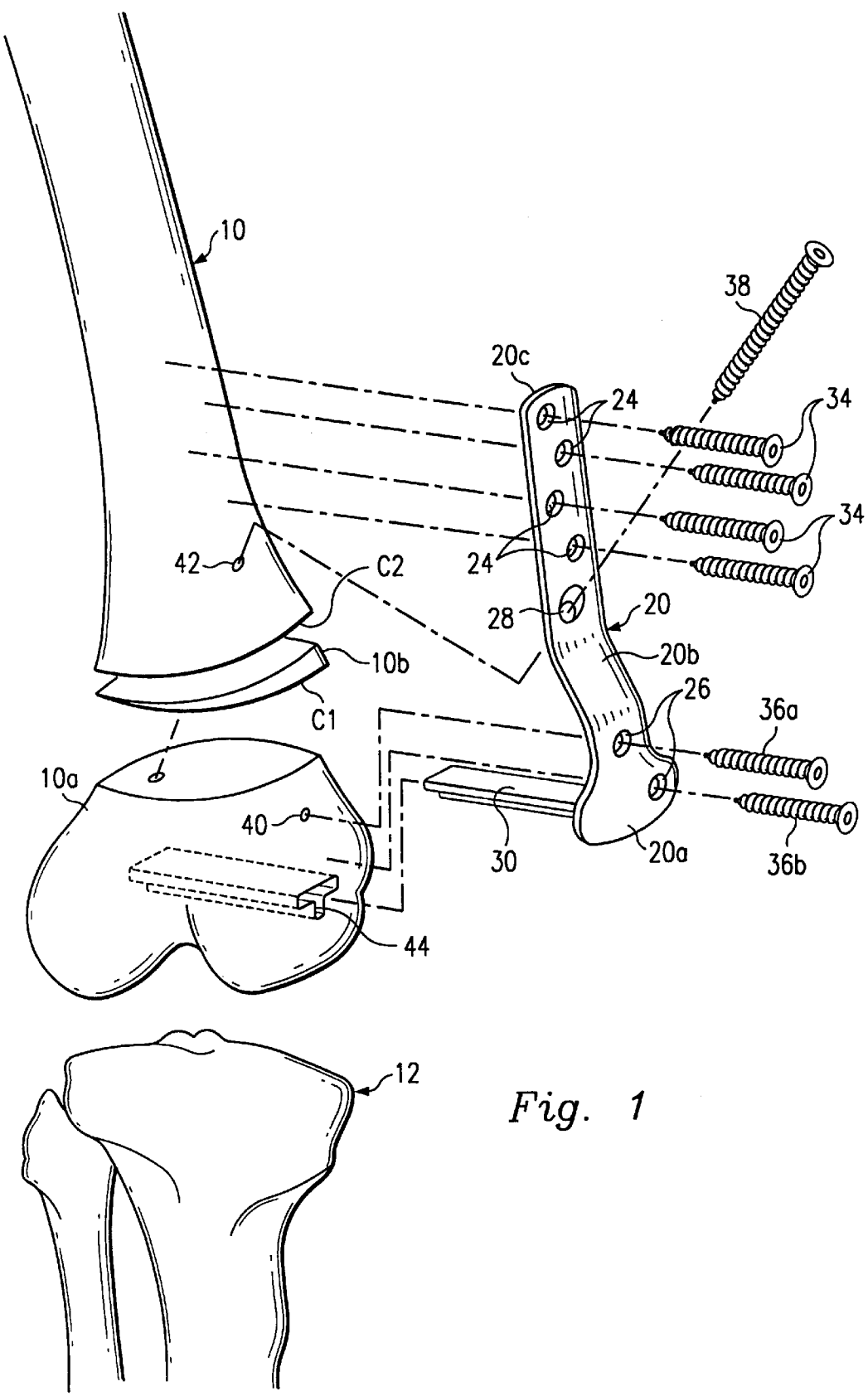
FIG. 1 is an exploded isometric view of an embodiment of the system shown with a femur and a tibia.

Referring to FIG. 1 of the drawing, a femur is referred to, in general, by the reference numeral 10 and is shown in a spaced relation to a tibia 12 for the purposes of illustration. In the latter context, it is understood that the lower end of the femur 10 is normally connected to the upper end of the tibia 12 by a patella, ligaments, and soft tissue which are not shown.

The present system and method are directed towards correcting for malalignment of the anatomical axis and the mechanical axis along the femur 10 and the tibia 12 in the coronal plane. To this end, according to the procedure of the present invention, an end segment 10a and a wedge-shaped segment 10b are cut from the distal end portion of the condylar portion of the femur 10 using standard osteotomy procedures involving a template, a guide assembly and cutting jigs. More particularly, a transverse cut C1 is made along the plane between the segments 10a and 10b but not completely through the femur 10. Then an angled cut C2 is made, preferably at an angle between 5 degrees and 10 degrees to the transverse cut, depending on the amount of malalignment. The angled cut C2 is initiated at the same side of the femur 10 as the transverse cut C1 and extends through the end of the transverse cut and on from the latter end until the segments 10a and 10b are severed from the femur. Since this technique is fully disclosed in the two above-identified patents, and utilizes the same hardware (with the exception that the procedure taught in the patents is directed to the tibia and the cuts are not completely through the tibia), it will not be described in any further detail.

After the above cuts, the wedge-shaped segment 10b is discarded and is therefore shown by dashed lines in FIG. 1.

Figure 2:
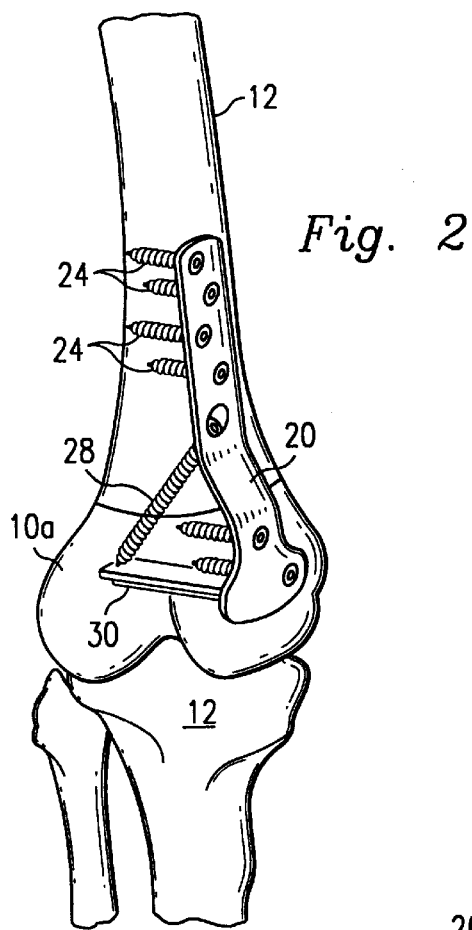
FIG. 2 is a view similar to FIG. 1 but depicting an embodiment of the system attached to the femur.
Figure 5:
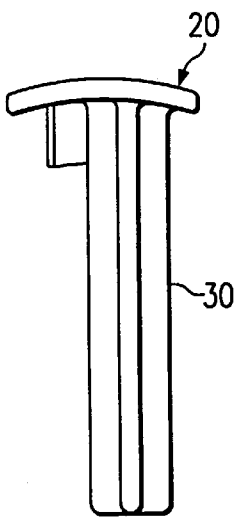
FIGS. 3–5 are elevational views of the plate used in the system of FIGS. 1 and 2.
Figure 3:
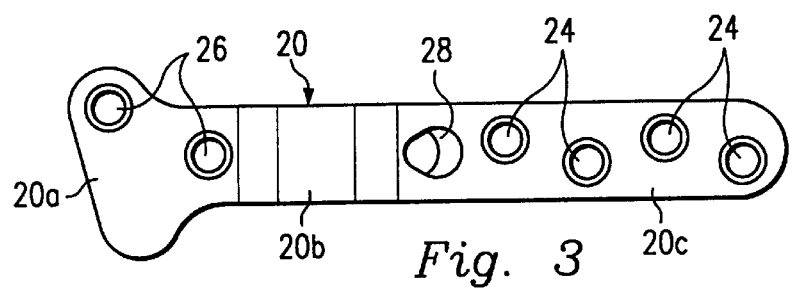
Figure 4:
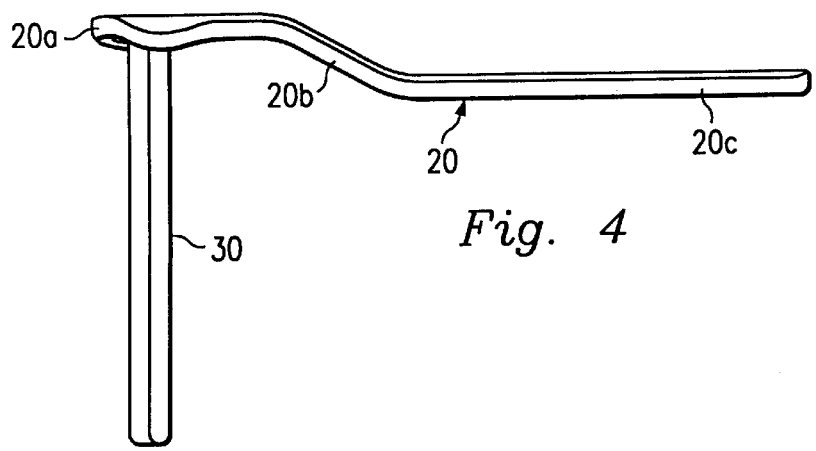

The segment 10a is placed back in its original position relative to the remaining portion of the femur 10 (said remaining portion hereinafter being referred to as the "femur"), with the removal of the wedge-shaped segment 10b correcting for the malalignment. The femur 10 is then attached to the segment 10a as shown in FIG. 2. To this end, a plate 20 is provided which is shown in detail in FIGS. 3–5. More particularly, the plate 20 has a flat end portion 20a that has an enlarged width, an angled portion 20b (FIG. 4) that extends from the end portion 20a, and a flat portion 20c that extends from the angled portion 20b to the other end of the plate.

Four through openings 24 (FIG. 3) are formed through the flat portion 20c of the plate 20 and extend perpendicular to the longitudinal axis of the plate, and two through openings 26 are formed through the end portion 20a of the plate 20 and extend perpendicular to the longitudinal axis of the plate. One angled opening 28 also extends through the flat plate portion 20c adjacent the angled plate portion 20b and approximately midway between the ends of the plate. The function of the openings 24, 26, and 28 will be described in detail.

A blade 30, having a T-shaped cross-section, is connected to the end portion 20a of the plate 20 in any conventional manner. The function of the blade 30 will also be described in detail.

As better shown in FIG. 1, four screws 34 are provided for extending through the openings 24 in the flat portion 20c of the plate 20, two screws 36a and 36b are provided for extending through the openings 26 in the enlarged plate portion 20a, and a screw 38 is provided for extending through the angled opening 28 in the plate portion 20c.

Prior to the attachment of the segment 10a to the femur 10, a transverse opening 40 is predrilled through the segment 10a for receiving the screw 36a, and an oblique opening 42 is predrilled through the femur 10 and into the segment 10a for receiving the screw 38. The screws 34 and the screw 36b are self-tapping and, as such, create corresponding openings when they are driven into the femur 10 and the segment 10a, respectively. Also, a slot 44 is punched into the segment 10a in any known manner for receiving the blade 30.

In accordance with the specific method of the present embodiments, a guide bracket, or the like (not shown) is placed across the femur 10, the hole 40 and the slot 44 are formed into the segment 10a and the hole 42 is formed through the femur 10 and into the segment 10a as described above. The guide bracket is then removed and the cuts C1 and C2 are made to define the end segment 10a and the wedge-shaped segment 10b. The segment 10b is discarded and the blade 30 is inserted in the slot 44 in the segment 10a. The screws 36a and 36b are then advanced through the openings 26 in the plate 10 and into the segment 10a in a direction perpendicular to the axis of the segment, with the screw 36a extending in the predrilled opening 40, to attach the plate to the segment.

The segment 10a is then positioned relative to the femur 10 until their corresponding ends butt and the femur 10 is realigned relative to the segment 10a in the position shown in FIG. 2 to correct for the malalignment. This realignment involves a slight tilting of the axis of the femur 10 from it original position relative to the segment 10 at an angle corresponding to the angle of the second cut C2 described above. In this position, the plate 20 bridges the junction between the femur 10 and the segment 10a, with the angled portion 20b of the plate accommodating the curvature of the segment 10a and the femur 10.

The segment 10a and the femur 10 are then compressed and held together by an external compressor device (not shown), such as the one disclosed in the above-identified patents, while the four screws 36 are driven through the holes 24 in the plate 20 and into the femur in a direction substantially perpendicular to the axis of the femur. The screw 38 is then driven through the angular hole 28 in the plate 20, and through the angular opening 42 extending through the femur 10 and into the segment 10a with the end of the screw extending to the distal end of the blade 30 as shown in FIG. 2. The plate 20 and the blade 30 thus establish a compressive load across the femur 10 and the segment 10a. The above-mentioned compressor device is removed, and the tibia 12 is repositioned relatively to the femur 10 with minimal disturbance of the patella, ligaments, soft tissue, and the like (not shown), and the femur and the segment 10a are allowed to heal.

As a result, one embodiment includes a system for providing compressive loading across an osteotomy site between two bones in an abutting relationship. The system includes a plate having a blade connected and extending at an angle to the plate. The plate extends across the osteotomy site with the blade extending in an opening of one of the bones. At least one fastener extends through openings in the plate and into at least one of the bones to fasten the plate to the bones and secure the blade in the opening.

Another embodiment provides a method for realigning an angularly malaligned bone including cutting an end segment from the bone, cutting a wedge-shaped segment from the bone, discarding the wedge-shaped segment, repositioning the bone and the end segment to correct for the malalignment, and establishing a compressive load across the remaining bone portion and end segment.

A further embodiment includes a plate for providing a compressive loading across an osteotomy site between a bone and a bone segment in abutting relationship. The plate has a flat portion and a curved portion. The curved portion is angled relative to the flat portion. The plate extends across the osteotomy site. A blade extends from the plate and into an opening in the bone segment. Fasteners attach the plate to the bone and the bone segment.

Several advantages result from the system and method of the present embodiments. For example, leg malalignment is corrected in a relatively simple and easy manner, while providing even compressive loading across the osteotomy site and improved bone healing. Also, the system can be left permanently attached as shown and described since it maintains a low profile and thus reduces complications with soft tissue closure and irritation. Further, any mismatching of osteotomy surfaces, and a consequent mismatching of cortical margins, is avoided. Still further, relative lateral translation of the segment 10a and the femur 10 is minimized. Also, the method of the present invention is easy to reproduce and is therefore predictable and can be completed with minimal disturbance to the patella, ligaments, and soft tissue.

It is understood that variations may be made in the foregoing without departing from the scope of these embodiments. For example, the angle that the portion 20b of the plate 20 makes with the other portions 20a and 20c can vary from that shown in FIG. 3. Also, the number and location of the screws 34, 36 and 38 can vary within the scope of the invention. Further, the present embodiments are not limited to use with the femur but can also be used to correct for malalignment of other bones, such as that caused by neck fractures, and the like.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A system for providing compressive loading across an osteotomy site between two bone segments in an abutting relationship, the system comprising a plate, a single blade having a T-sharped cross section and being connected to one end of the plate and extending at an angle to the plate, the plate adapted to extend across the osteotomy site with the blade extending in an opening formed in one of the bone segments, at least one fastener extending through openings in the plate and, adapted to extend into at least one of the bone segments to fasten the plate to the bone segments and secure the blade in the opening.

2. The system of claim 1 wherein the blade has a smooth outer surface.

3. The system of claim 2 wherein the blade has a non-tapering configuration.

4. The system of claim 3 wherein the blade has an elongated and straight configuration.

5. The system of claim 4 wherein the blade is rigid and permanently attaches to the plate.

6. The system of claim 1 wherein the opening is non-circular and formed as a slot punched into the second bone segment, and the blade is adapted to be inserted into the opening.

7. A method for realigning an angularly malaligned bone, comprising the steps of cutting an end segment from the bone, cutting a wedge-shaped segment from between the end segment and the remaining portion of the bone, the wedge-shaped segment having an angled surface substantially corresponding to the angle of malalignment, discarding the wedge-shaped segment, forming a non-circular opening in the end segment, repositioning the end segment relative to the remaining portion of the bone at an angle corresponding to the angle of malalignment to realign the end segment and the remaining bone portion and correct for the malalignment, inserting a blade having a non-tapering configuration into the opening and positioning a plate across the bone portion and end segment to establish a compressive load across the bone portion and end segment.

8. The method of claim 7 wherein the first step of cutting is at an angle substantially traverse to the longitudinal axis of the bone, and wherein the second step of cutting is at an angle substantially corresponding to the angle of malalignment to form the angled surface.

9. The method of claim 7 further comprising the steps of fastening a first end of the plate to the blade, and fastening a second end of the plate to the remaining bone portion.

10. The method of claim 9 further comprising the step of fastening the first end of the plate to the end segment.

11. A plate for providing compressive loading across an osteotomy site between a first bone segment and a second bone segment in abutting relationship comprising:

a plate having a flat portion and a curved portion, the curved portion being angled relative to the flat portion;

the plate adapted to extend across the osteotomy site;

a single blade extending from one end of the plate and adapted to be inserted into an opening formed in the second bone segment, the blade having a smooth outer surface with a T-shaped cross section; and fasteners attaching the plate to the first and second bone segments.

12. The plate as defined in claim 11 wherein the blade is permanently connected to the plate and has an elongated, rigid shape adapted to provide even compressive load across the osteotomy site.

13. The plate as defined in claim 11 wherein the opening is non-circular and formed as a slot punched into the second bone segment, and the blade is adapted to be inserted into the opening.

* * * * *